United States Patent [19]
Harada et al.

[11] Patent Number: 5,693,485
[45] Date of Patent: Dec. 2, 1997

[54] ENZYMATIC COUPLING REACTION OF N-PROTECTED-L-ASPARTIC ACID AND PHENYLALANINE METHYL ESTER

[75] Inventors: Tsuneo Harada; Shigeaki Irino; Yukio Kunisawa, all of Yamaguchi-ken; Kiyotaka Oyama, Tokyo-to, all of Japan

[73] Assignee: Holland Sweetener Company V.o.F., Maastricht, Netherlands

[21] Appl. No.: 729,507

[22] Filed: Oct. 11, 1996

[30] Foreign Application Priority Data

Oct. 11, 1995 [EP] European Pat. Off. .............. 95202744

[51] Int. Cl.⁶ .............. C12P 21/00; C12P 21/02; C07K 5/06
[52] U.S. Cl. .......... 435/68.1; 435/212; 435/213; 435/219; 530/333; 560/38; 560/40; 560/41
[58] Field of Search .................... 435/68.1, 212, 435/213, 219; 560/38, 40, 41; 530/333

[56] References Cited

U.S. PATENT DOCUMENTS

| | | | |
|---|---|---|---|
| 4,284,721 | 8/1981 | Oyama et al. | |
| 4,436,925 | 3/1984 | Isowa et al. | 560/19 |
| 4,487,717 | 12/1984 | Oyama et al. | 560/32 |
| 4,521,514 | 6/1985 | Oyama et al. | 435/68.1 |
| 4,873,359 | 10/1989 | Chmurny et al | 560/40 |
| 5,002,872 | 3/1991 | Gross | 435/68.1 |
| 5,279,946 | 1/1994 | Su et al. | |
| 5,418,146 | 5/1995 | Joo et al. | 435/68.1 |

FOREIGN PATENT DOCUMENTS

A2 2 453 137  10/1980  France.

OTHER PUBLICATIONS

Database WPI, Section Ch, Week 8531, Derwent Publications Ltd., London, GB, Class A96, JP–A–60–118190 (Jun. 1995), AN 85–188004, Abstract.

*Primary Examiner*—Herbert J. Lilling
*Attorney, Agent, or Firm*—Cushman, Darby & Cushman IP Group of Pillsbury Madison & Sutro LLP

[57] ABSTRACT

The invention relates to a process for the preparation of N-protected-L-aspartyl-L-phenylalanine methyl ester by enzymatic coupling of an N-protected-L-aspartic acid and L- or DL-phenylalanine methyl ester in an aqueous solution with formation of a precipitate using a thermolysin-like protease enzyme, wherein a water-immiscible organic solvent is added to and blended with the reaction system during the formation of the precipitate in the course of the coupling reaction, which organic solvent has a relatively high affinity for the precipitate. The process is particularly suitable as a continuous process. The method results in lower enzyme deactivation during and after the enzymatic coupling reaction and in larger and thicker precipitated crystals.

18 Claims, No Drawings ns # ENZYMATIC COUPLING REACTION OF N-PROTECTED-L-ASPARTIC ACID AND PHENYLALANINE METHYL ESTER

BACKGROUND TO THE INVENTION

1. Field of the Invention

The invention relates to a process for the preparation of N-protected-L-aspartyl-L-phenylalanine methyl ester by enzymatic coupling of an N-protected-L-aspartic acid and L- or DL-phenylalanine methyl ester in an aqueous solution with formation of a precipitate using a thermolysin-like protease enzyme. The invention also relates to such a continuous process for the preparation of N-protected-L-aspartyl-L-phenylalanine methyl ester by enzymatic coupling of an N-protected-L-aspartic acid and L- or DL-phenylalanine methyl ester in an aqueous solution with formation of a precipitate using a thermolysin-like protease enzyme.

2. Description of the Related Art

Aspartame, the α-dipeptide ester L-aspartyl-L-phenylalanine methyl ester (hereinafter also referred to as APM), is an important synthetic low-calorie sweetening agent which is about 200 times as sweet as sugar and has an exceptionally good taste pattern without, for instance, a bitter aftertaste. The sweetener is used as such in a wide range of products such as soft drinks, sweets, table-top sweeteners, pharmaceutical products and the like.

Aspartame can be prepared by various known routes. U.S. Pat. No. 4,212,945 describes the enzymatic coupling reaction of an N-protected-L-aspartic acid (X-Asp) and L- or DL-phenylalanine methyl ester (PM) in an aqueous medium with formation of a precipitate in the presence of a thermolysin enzyme. In that case the precipitate is an addition compound of X-APM (the coupling product of X-Asp and PM) and PM. Certain precipitates thus are useful as intermediates in the production of aspartame. Formation of a precipitate during the enzymatic coupling reaction is advantageous, since the equilibrium of the coupling reaction is thereby shifted towards the desired coupling product.

It is known that, when the enzymatic coupling reaction is carried out with stirring, the enzyme activity is lowered noticeably and recovery of active enzyme is therefore unsatisfactory. In order to overcome such a disadvantage it has been proposed in Japanese Patent Application Laid-Open No. 55-19051 to carry out the enzymatic coupling reaction without stirring, that is to say, statically. However, this method is disadvantageous since the precipitation of product results in the formation of a more or less completely solidified reaction mixture and the recovery of enzyme as captured in the entangled crystals is very difficult.

For recovery of the enzyme various methods are known: (i) a method in which the reaction mixture is filtered, after the reaction, to isolate and recover the solid precipitate from the aqueous phase containing non-reacted starting materials and enzyme; (ii) a method in which a water-immiscible organic solvent is added to the reaction mixture, which is capable of dissolving and extracting the precipitate, so that the original precipitate is recovered from the organic phase and the enzyme from the aqueous phase, respectively (Japanese Patent Application Laid-Open No. 54-11295); and (iii) a method in which a water-immiscible organic solvent having low solubility for the precipitate is added to the reaction system and the precipitate is isolated by solid liquid separation, whereafter the enzyme is recovered from the aqueous phase (Japanese Patent Publication No. 2-12238). The precipitated product then is converted into APM by steps including the removal of the protective group by methods known per se. The recovered enzyme is preferably re-used in the next coupling reaction.

However, in all cases above, enzyme recovery from the reaction slurries etc. is not satisfactory. It has been observed, upon recovery of enzyme, that strong enzyme deactivation takes place during and after the coupling reaction using thermolysin-like protease enzyme. The performance of such an enzyme thus is insufficient, which, economically, is a serious problem. Moreover, all processes mentioned above require a batchwise enzymatic coupling reaction. Accordingly, there existed a strong need for providing a process which significantly reduces the effects of enzyme deactivation during and after coupling reaction (without significant negative effects on the coupling reaction itself) and which, moreover, would make it possible to carry out the process for enzymatic coupling of X-Asp and PM in a continuous way.

SUMMARY OF THE INVENTION

The inventors have made detailed studies with respect to the deactivation of thermolysin-like protease enzyme during and after the coupling reaction. Solving this problem by ordinary methods, such as, for example, by controlling or adjusting the stirring conditions, reaction temperature and reaction time, turned out to be very difficult.

Surprisingly, it now has been found that it is possible to improve the process for the preparation of N-protected-L-aspartyl-L-phenylalanine methyl ester by enzymatic coupling of an N-protected-L-aspartic acid and L- or DL-phenylalanine methyl ester in an aqueous solution with formation of a precipitate using a thermolysin-like protease enzyme, if a water-immiscible organic solvent is added to and blended with the reaction system during the formation of the precipitate in the course of the coupling reaction, the organic solvent having a relatively high affinity for the precipitate.

This result is, amongst other things, surprising since it is widely accepted that addition of an organic solvent tends to lower the enzymatic activity of the enzyme used noticeably. The inventors now have found that addition of a water-immiscible organic solvent, even when applied in small amounts, during the course of the enzymatic coupling reaction of X-Asp and PM leads to significant improvement of the performance of the enzyme used in that recovery of active enzyme is increased without any substantial negative effect on the coupling reaction itself. In addition, it has, surprisingly, been found that crystal particles formed during the coupling reaction are larger and thicker than in case no organic solvent is added; this is favourable in the solid-liquid separation step required.

Thus, the process for the preparation of N-protected-L-aspartyl-L-phenylalanine methyl ester by enzymatic coupling of an N-protected-L-aspartic acid and L- or DL-phenylalanine methyl ester in an aqueous solution with formation of a precipitate using a thermolysin-like protease enzyme is substantially improved.

Without committing themselves to one specific theory, the inventors now believe the improved performance of the enzyme may be due to a combination of the following factors: (i) in the absence of the organic solvent adsorption of enzyme occurs to the precipitate being formed progressively during the course of the reaction; this effect seems to be very pronounced during a static coupling reaction; and (ii) in the absence of the organic solvent serious deactivation of the enzyme in adsorbed form occurs under mechanical influences of stirring when the viscosity of the reaction system tends to increase strongly during the middle and last stages of the coupling reaction. Both effects may strongly influence the enzyme performance.

The present invention therefore relates to a process for the preparation of N-protected-L-aspartyl-L-phenylalanine methylester by enzymatic coupling of an N-protected-L-aspartic acid and L- or DL-phenylalanine methyl ester in an aqueous solution with formation of a precipitate using a thermolysin-like enzyme, wherein a water-immiscible organic solvent is added to and blended with the reaction system during the formation of the precipitate in the course of the coupling reaction, the organic solvent having a relatively high affinity for the precipitate.

As used herein, aqueous solution means a solution in water. As used herein, thermolysin-like protease enzyme means any neutral metalloprotease enzyme having peptide coupling activity in the formation of X-APM, for instance, the nprM gene from *Bacillus stearothermophilus* (Kubo, J. Gen. Microbiol. 134, 1883–92 (1988)) or from *Bacillus thermoproteolyticus*, or suitable mutants thereof; these enzymes are commercially available, e.g. from Amano and from Daiwa. As L-aspartic acid N-protective groups suitable for use in the present process can be named, for example, benzyloxycarbonyl, benzyl, acetyl, formyl, p-methoxybenzyloxycarbonyl, and t-butoxycarbonyl. Preferably, benzyloxycarbonyl ("Z") is used as the N-protecting group. The reaction temperature during the enzymatic coupling reaction usually is in the range of 5 to 50° C.

The water-immiscible organic solvents to be added to and blended with the reaction system during the formation of the precipitate in the course of the coupling reaction form a second liquid phase under the reaction conditions (e.g. at the concentration of reactants, salt, etc. as present) and should have a relatively high affinity for the precipitate. Relatively high affinity for the precipitate as used here is intended to mean that the organic solvent, if added in small amounts to the aqueous reaction system, preferentially tends to surround the precipitated particles. The organic solvent may be a good solvent for the precipitate, when used in larger amounts, but it is preferred that the solubility of the precipitate in the organic solvent, at the temperature chosen, is rather low. Suitable examples of organic solvents which can be used in the present invention are, for instance, aromatic hydrocarbons, such as benzene or toluene, $C_{3-6}$ ketones, such as methylisobutylketone (MIBK) or diisobutylketone, $C_{3-6}$ alcohols, such as isopropanol and t-butanol, $C_{1-6}$ hydrocarbon halides, such as chloroform or 1,3-dichloropropane, and $C_{2-10}$ esters, as well as mixtures thereof. Organic solvents having a higher affinity for the precipitate are preferred. Toluene has the highest affinity for the precipitate, and is therefore most preferred. MIBK is also preferred, since this solvent can be applied in even smaller amounts than toluene and gives very good separation of the aqueous and organic layers, and crystal particles are very large.

In accordance with the present invention the water-immiscible organic solvent should be added to and blended with the reaction system during the formation of the precipitate in the course of the coupling reaction, i.e. after some precipitate has already been formed. Adding and blending is important for ensuring that the organic solvent preferentially surrounds the precipitated particles. It is surprising that very large crystal particles are formed during the course of the coupling reaction.

In accordance with the present invention only a small amount of the organic solvent needs to be added to the slurry mixture of the reaction system in order to achieve good results. The amount of organic solvent to be used, however, is not strictly limited. The skilled man will easily be able to find which amount is suitable for the desired purpose; this will, inter alia, depend on the choice of the organic solvent. Preferably, the amount of organic solvent added during the coupling reaction is from 0.01 to 1.0 part by weight relative to one part by weight of the sum of X-Asp and PM being used in the coupling reaction. In general, the amount of X-Asp and PM used in the coupling reaction will be in the range of 10 to 30% by weight of the total reaction system. If larger amounts of organic solvent are used, an undesired lowering of the reaction rate and inactivation of enzyme may take place, and more precipitate will dissolve, thus requiring more difficult working up of the reaction mixture.

Addition to and blending with the reaction mixture of the water-immiscible organic solvent should be started at the latest when the conversion of the coupling reaction has reached about 85%, because at that time the effects of deactivation of the enzyme already are irreparably large and the viscosity of the slurry will have risen to a very high value, which results in low enzyme recovery. Even more preferably, addition and blending should be started before a conversion of about 75% has been reached.

On the other hand, addition and blending should not be started before the conversion of the coupling reaction has reached about 10%, at which time sufficient precipitate will have formed. It is preferred to start the addition and blending of the water-immiscible organic solvent even at a later stage, preferably when conversion has reached about 25% or 30%, and even more preferably when it has reached about 50%. In the earliest stages of the reaction, i.e. before conversion has reached about 30%, adsorption of the enzyme onto the precipitate is still rather low and it is preferred to maintain the enzyme activity during this stage at the highest possible level, that is without any lowering of the reaction rate due to the presence of the organic solvent. If the organic solvent would be present in the reaction mixture already from the start of the coupling reaction, the starting material PM would be preferentially transferred to the organic phase, which would lead to undesired lowering of the reaction rate and/or additional feeding of PM and pH control.

When the organic solvent chosen according to the present invention is toluene or methylisobutylketone, addition to and blending with the reaction mixture is preferably started when the conversion of the coupling reaction has reached from about 30% to 75% in order to achieve the best results in terms of reaction rate and enzyme recovery combined. In cases where relatively high concentrations of reactants are used in the coupling reaction, adding and blending is preferably started in the lower part of said 30% to 75% conversion range, e.g. from about 30% to 60%. At relatively low concentrations of reactants, the addition and blending of the organic solvent is preferably started after conversion has reached from about 50% to 75%.

Toluene is preferably added in an amount of from 0.2 to 0.5 part by weight relative to one part by weight of the sum of X-Asp and PM being used in the coupling reaction. Methylisobutylketone can be applied in even smaller amounts than toluene, and is preferably added in an amount of from 0.1 to 0.3 part by weight relative to one part by weight of the sum of X-Asp and PM being used in the coupling reaction.

The temperature at the time when the organic solvent is added to the reaction system is not particularly limited, provided that it does not interfere with the reaction itself, which, as indicated above, is usually in the range of 5° to 50° C.

After the coupling reaction the organic phase and precipitate are separated by known methods from the enzyme containing aqueous phase, which also contains the major part of the remainder of non-reacted starting materials; the latter phase in principle can be re-used in a further coupling reaction process, if desired with fresh enzyme being supplemented. After reaction, the enzyme can be recovered by known methods such as filtration, extraction, etc. The precipitate, and any X-APM dissolved in the organic phase, can be converted to the desired product APM.

The water-immiscible organic solvent added to and blended with the reaction system may be added at once or gradually, either in portions or continuously, as the reaction proceeds. Continuous addition and blending is especially preferred in case the coupling reaction is performed, as has now been made feasible by the present invention, in a continuous way. The coupling reaction thus may be performed batchwise or continuously. Continuous operation may take place in one reactor, or in a number of reactors in series (i.e. in a multi-reactor process).

In a preferred embodiment of this invention the water-immiscible organic solvent is continuously added to and blended with the reaction system of a continuously operated enzymatic coupling process, while precipitate is being formed. In such a continuous process for the enzymatic coupling a steady state is reached in the coupling reactor or reactors by simultaneously, and (semi-)continuously, adding fresh aqueous solution of starting materials (and supplying enzyme) and withdrawing an amount of the slurry from the reactor(s) which is about equal to that of the aqueous solution supplied. In case a multi-reactor process is chosen, the organic solvent is preferably fed continuously into the first and/or further reactor(s) of the multi-reactor system.

The average amount of organic solvent added per hour during the coupling reaction, according to the present invention in a continuous coupling process, is preferably from 0.01 to 1.0 part by weight relative to one part by weight of the sum of X-Asp and PM on average being used per hour in the continuous coupling reaction. More preferably, in the continuous process addition to and blending with the reaction mixture of the organic solvent is started at the latest when the conversion of the continuous coupling reaction first (that is, during the start-up of the continuous process) has reached about 85%, more particularly not before it first has reached about 10%.

Very favourable results are achieved in a continuous coupling process when the organic solvent added is toluene or methylisobutylketone and addition to and blending with the reaction mixture of the organic solvent is started when the conversion of the coupling reaction first has reached from about 30% to 75%. If the organic solvent used is toluene, it is preferably added in an average amount per hour of from 0.2 to 0.5 part by weight relative to one part by weight of the sum of X-Asp and PM on average being used per hour in the continuous coupling reaction. If the organic solvent is MIBK it is preferably added in an average amount per hour of from 0.1 to 0.3 part by weight relative to one part by weight of the sum of X-Asp and PM on average being used per hour in the continuous coupling reaction.

Toluene and/or MIBK are preferably fed into the first (and/or further) reactor(s) of a multi-reactor continuous process. This is done especially in case the conversion in the first reactor is maintained at about 50% or higher, because this allows for achieving of very high conversions, of about 90–95% or higher, in the multi-reactor process.

The present invention will be explained in more detail by way of the following examples, which, however, are not intended to restrict the scope of the present invention in any way.

In the following Examples and Comparative Experiments conversions, calculated on the basis of Z-Asp used, were determined by high performance liquid chromatography on a TSK-gel 2000SW column from Tosoh Corporation. For that purpose small samples from the reaction mixture were taken at regular intervals, the last sample being taken from the final reaction mixture suspension. For the Examples indications of crystal dimensions were gathered by microscopic evaluation (at 100x magnification) of samples withdrawn during and after the reaction, and/or by laser radiation measurement of the mean value (M.V.) of the particle size distribution using a Microtruck FRA instrument from Leads & Northrup. The crystal sizes referred to in the Examples represent M.V. values, and thus give an indication of average length and thickness.

The stirring torque of the reaction mixture suspension was determined by using an agitator which was equipped with a torque meter. The final torque is the torque at the end of the experiment. For the enzyme retention percentage, the slurry was sampled at the end of the coupling reaction and analyzed by high pressure liquid chromatography (hplc) the activity of the remaining enzyme was then calculated as a percentage of the activity of the original enzyme preparation at the start of the reaction. This was determined by hplc on a TSK-gel Phenyl-5PW RP column from Tosoh Corporation.

EXAMPLE 1

1930 g of a solution of N-benzyloxycarbonyl-L-aspartic acid (Z-Asp; 2.0 mols; 534 g) in water (1396 g), 2989 g of a solution of DL-phenylalanine methyl ester (DL-PM; 5.0 mols; 895 g) in water (2094 g), and 146 g of a 22% (wt.) aqueous sodium hydroxide solution were filled into a 20 1 glass reactor equipped with a stirrer and thermostatted at 40° C. To this mixture an enzyme solution was added which had been prepared by dissolving 240 g of sodium chloride, 7.5 g of calcium chloride dihydrate and 30 g of crude thermolysin (Thermoase PS-160, trade name of Daiwa Chemical Co.) in 2200 g of distilled water. The enzymatic coupling reaction was then carried out at 40° C. with stirring.

During the coupling reaction the addition product of α-N-benzyloxycarbonyl-L-aspartyl-L-phenylalanine methyl ester and D-phenylalanine methyl ester (Z-APM.D-PM) precipitated. After 11 hours of reaction, the conversion of the reaction (calculated on Z-Asp) having reached about 55% as determined by hplc, 176 g of toluene (that is, 0.145 part by weight relative to one part by weight of the sum of Z-Asp+DL-PM) was added to the reaction system at once. The reaction was continued with stirring until no significant further conversion could be observed by hplc; at that time 18 hours had passed since the start of the reaction.

The torque of the reaction mixture was determined during the reaction by using an agitator equipped with a torque meter; the final torque was 169 Ncm. Further, the molar yield of precipitated Z-APM.D-PM was calculated to be 92.2%. The enzyme retention percentage was 81.5%. From evaluation of samples taken just before addition of toluene and at the end of the reaction it was observed that large crystal particles of the precipitate were formed after addition of toluene. The average crystal size (M.V.) was 22 μm.

COMPARATIVE EXPERIMENT A

The process of Example 1 was repeated, except that 32 g of thermolysin was used and that no toluene was added. In this Comparative Example the enzymatic reaction came to a stop after 17 hours of reaction.

The reaction mixture suspension was then collected and the final torque thereof was found to be 224 Ncm; the molar yield of precipitated Z-APM.D-PM was calculated to be 93.5%. The enzyme retention percentage, however, was only 34.7%. From microscopic evaluation of samples taken after 11 and 17 hours it was observed that the average size of the crystals was much smaller than 10 μm.

EXAMPLE 2

The process of Example 1 was repeated, except that after 11 hours of reaction 353 g of toluene (that is, 0.29 part by weight relative to one part by weight of the sum of Z-Asp+DL-PM) was added to the reaction system at once. The conversion of the reaction at the time of the toluene addition had reached about 69%. The reaction was continued with stirring until no significant further conversion could be observed; at that time 19 hours had passed since the start of the reaction.

The reaction mixture suspension was then collected and the final torque thereof was found to be 80 Ncm; the molar yield of precipitated Z-APM.D-PM was calculated to be 93.9%. The enzyme retention percentage was 89.9%. The average crystal size was 65 μm.

EXAMPLE 3

The process of Example 2 was repeated, except that the addition of 353 g of toluene was done after 13 hours of reaction. The conversion of the reaction at the time of the toluene addition had reached about 82%. The reaction was continued with stirring until no significant further conversion could be observed; at that time 19 hours had passed since the start of the reaction.

The reaction mixture suspension was then collected and the final torque thereof was found to be 135 Ncm; the molar yield of precipitated Z-APM.D-PM was calculated to be 93.5%. The enzyme retention percentage was 82.9%. The average crystal size was about 100 μm.

EXAMPLE 4

The process of Example 2 was repeated, except that 353 g of methylisobutylketone (MIBK) was added instead of toluene; addition took place at once after 11 hours of reaction, and the conversion of the reaction at that time had reached about 69%. The reaction was continued with stirring until no significant further conversion could be observed; at that time 22 hours had passed since the start of the reaction.

The reaction mixture suspension was then collected and the final torque thereof was found to be 78 Ncm; the molar yield of precipitated Z-APM.D-PM was calculated to be 92.5%. The enzyme retention percentage was 89%. The average crystal size was 53 μm.

EXAMPLE 5

1929 g of a solution of Z-Asp (2.0 mols; 534 g) in water (1395 g), 3153 g of a solution of DL-PM (5.0 mols; 895 g) in water (2258 g), and 150 g of a 22% (wt.) aqueous sodium hydroxide solution were filled into a 20 l glass reactor, equipped with a stirrer and thermostatted at 40° C. To this mixture an enzyme solution was added which had been prepared by dissolving 200 g of sodium chloride, 7.0 g of calcium chloride dihydrate and 42 g of protease TD (product of Amano Pharmaceutical Co.) in 2050 g of distilled water. The enzymatic coupling reaction was then carried out at 40° C. with stirring.

During the coupling reaction Z-APM.D-PM precipitated. After 8 hours of reaction, the conversion of the reaction (calculated on Z-Asp) having reached about 65%, 176 g of a 90/10 w/w mixture of MIBK and toluene (that is, 0.145 part by weight relative to one part by weight of the sum of Z-Asp+DL-PM) was added to the reaction system at once. The reaction was continued with stirring until no significant further conversion could be observed by hplc; at that time 16 hours had passed since the start of the reaction.

The reaction mixture suspension was then collected and the final torque thereof was found to be 84 Ncm; the molar yield of precipitated Z-APM.D-PM was calculated to be 91.8%. The enzyme retention percentage was 86.5%. The average crystal size was about 30 μm.

COMPARATIVE EXPERIMENT B

The process of Example 5 was repeated, except that 32 g of protease TD was used and that no MIBK/toluene was added. In this Comparative Experiment the enzymatic reaction came to a stop after 16 hours of reaction.

The reaction mixture suspension was then collected and the final torque thereof was found to be 243 Ncm; the molar yield of precipitated Z-APM.D-PM was calculated to be 92.1%. The enzyme retention percentage, however, was 62.7%. The average crystal size was much smaller than 10 μm.

EXAMPLE 6

286 g of a solution of Z-Asp (0.4 mols; 107 g) in water (179 g), 598 g of a solution of DL-PM (1.0 mol; 179 g) in water (419 g), and 29.2 g of a 22% (wt.) aqueous sodium hydroxide solution were filled into a 2 l glass reactor, equipped with a stirrer and thermostatted at 40° C. To this mixture an enzyme solution was added which had been prepared by dissolving 48 g of sodium chloride, 1.5 g of calcium chloride dihydrate and 16 g of crude thermolysin (Thermoase PS-160 of Daiwa Chemical Co. ) in 440 g of distilled water. The enzymatic coupling reaction was then carried out at 40° C. with stirring.

During the coupling reaction Z-APM.D-PM precipitated. After 3 hours of reaction, the conversion of the reaction (calculated on Z-Asp) having reached about 55%, 90 g of toluene (that is, 0.31 part by weight relative to one part by weight of the sum of Z-Asp +DL-PM) was added to the reaction system at once. The reaction was continued with stirring until no significant further conversion could be observed; at that time 9 hours had passed since start of the reaction.

The reaction mixture suspension was then collected and the final torque thereof was found to be 2.0 Ncm; the molar yield of precipitated Z-APM.D-PM was calculated to be 96.3%. The enzyme retention percentage was determined to be 99.3%. The average crystal size was 114 μm.

EXAMPLE 7

The process of Example 6 was repeated, except that after 3 hours of reaction, 60 g of toluene (that is, 0.21 part by weight relative to one part by weight of the sum of Z-Asp +DL-PM) was added to the reaction system at once. The reaction was continued with stirring until no significant further conversion could be observed; at that time 9 hours had passed.

The reaction mixture suspension was then collected and the final torque thereof was found to be 5.7 Ncm; the molar yield of precipitated Z-APM.D-PM was calculated to be 96.2%. The enzyme retention percentage was 92.7%. The average crystal size was 46 μm.

EXAMPLE 8

The process of Example 6 was repeated, except that after 3 hours of reaction, 30 g of toluene (that is, 0.1 part by weight relative to one part by weight of the sum of Z-Asp+ DL-PM) was added to the reaction system at once. The reaction was continued with stirring until no significant further conversion could be observed; at that time 9 hours had passed.

The reaction mixture suspension was then collected and the final torque thereof was found to be 11 Ncm; the molar yield of precipitated Z-APM.D-PM was calculated to be 96.2%. The enzyme retention percentage was 86.3%. The average crystal size was 20 μm.

EXAMPLE 9

The process of Example 6 was repeated, except that after 3 hours of reaction, 60 g of MIBK (that is, 0.21 part by weight relative to one part by weight of the sum of Z-Asp +DL-PM) was added to the reaction system at once. The reaction was continued with stirring until no significant further conversion could be observed; at that time 9 hours had passed.

The reaction mixture suspension was then collected and the final torque thereof was found to be 0.1 Ncm; the molar yield of precipitated Z-APM. D-PM was calculated to be 95.8%. The enzyme retention percentage was 94.1%. The average crystal size was 48 μm.

EXAMPLE 10

The process of Example 9 was repeated, except that after 3 hours of reaction, 90 g of MIBK (that is, 0.31 part by weight relative to one part by weight of the sum of Z-Asp +DL-PM) was added to the reaction system at once. The reaction was continued with stirring until no significant further conversion could be observed; at that time 9 hours had passed.

The reaction mixture suspension was then collected and the final torque thereof was found to be 2.1 Ncm; the molar yield of precipitated Z-APM.D-PM was calculated to be 93.8%. The enzyme retention percentage was 94.1%. The average crystal size was 71 μm.

EXAMPLE 11

The process of Example 9 was repeated, except that after 3 hours of reaction, 30 g of MIBK (that is, 0.1 part by weight relative to one part by weight of the sum of Z-Asp+DL-PM) was added to the reaction system at once. The reaction was continued with stirring until no significant further conversion could be observed; at that time 9 hours had passed.

The reaction mixture suspension was then collected and the final torque thereof was found to be 3.0 Ncm; the molar yield of precipitated Z-APM.D-PM was calculated to be 93.8%. The enzyme retention percentage was 87.5%. The average crystal size was 24 μm.

EXAMPLE 12

(Continuous mode)

A first reactor (glass; 3 l; equipped with stirrer; thermostatted at 40° C.) was filled with aqueous solutions of, respectively, Z-Asp (0.5 mol; 133.5 g in 338.5 g of water), DL-PM (1.25 mol; 224 g in 562 g of water) and 25% wt. sodium hydroxide (35 g solution), after which mixing took place. An aqueous enzyme solution containing 22.5 g of protease TD (Amano Pharmaceutical Co.), 63 g of sodium chloride and 0.64 g of calcium chloride dihydrate in 621 g of water was added thereto, to obtain 2000 g of reaction mixture. The reaction was continued for 3 hours and a Z-Asp conversion of 62% was reached.

In the meantime, separately, a solution of Z-Asp, DL-PM and sodium hydroxide starting materials (having the same composition as the contents of the first reactor before the enzyme solution was introduced) as well as a fresh enzyme solution of the same composition as the above protease TD solution were prepared in sufficient amounts so as to be able to feed a combined fresh reaction mixture (of the same composition as the initial 2000 g of reaction mixture) at a rate of 667 g/hour. When said combined feed to the first reactor was started, reaction mixture was simultaneously withdrawn, at the same rate as the feed, from the first reactor to a second reactor, also being stirred and operated at 40° C. Simultaneously, a feed of MIBK was introduced into the second reactor at a rate of 13.3 g/hour (that is, 0.11 part by weight relative to one part by weight of the sum of Z-Asp+DL-PM being used on average per hour in the continuous coupling reaction).

After about 3 hours of feeding raw materials to the first reactor and withdrawing reaction mixture from the first reactor to the second reactor with simultaneous feeding of MIBK thereto, slurry was also withdrawn from the second reactor to a receiving vessel at about the same rate as the feed. After an average residence time of 6 hours in the two reactors, the coupling reaction approximately reached an equilibrium in the receiving vessel.

This reaction system could easily be operated for more than 72 hours after the start of the reaction. Relevant results in the first and second reactor after 24 hours were:

|  | first reactor | second reactor |
| --- | --- | --- |
| Z-Asp conversion (in %) | 70.6 | 89.9 |
| enzyme retention (in %) | 95.0 | 92.5 |
| stirring torque (in Ncm) | 9.6 | 3.8 |

The final average size of crystals was estimated at about 150 μm or higher.

EXAMPLE 13

Example 12 was repeated, except that the mean residence times in the first and in the second reactor were now 4 hours, which was achieved by reducing the amount of feed to 500 g/hr, and that toluene, at a feed rate of 25 g/hr to the first reactor and at a feed rate of 5 g/hr to the second reactor, was used instead of MIBK. The feed rate of toluene corresponds to 0.42 part by weight relative to one part by weight of the sum of Z-Asp+DL-PM being used on average per hour in the continuous coupling reaction.

After 27 hours of reaction the following results were obtained in the first and the second reactor:

|  | first reactor | second reactor |
| --- | --- | --- |
| Z-Asp conversion (in %) | 77.6 | 94.3 |
| enzyme retention (in %) | 97.4 | 94.4 |
| stirring torque (in Ncm) | 2.0 | 4.9 |

The final average size of crystals was estimated at about 200 μm or higher.

COMPARATIVE EXPERIMENT C

The process of Example 13 was repeated, except that no organic solvent was supplied to the (second) reactor(s). The results after 24 hours of reaction were as follows:

|  | first reactor | second reactor |
|---|---|---|
| Z-Asp conversion (in %) | 76.6 | 90.2 |
| enzyme retention (in %) | 91.2 | 64.0 |
| stirring torque (in Ncm) | 14.7 | 14.7 |

Final average size of crystals was estimated at about 10 μm.

The above results can be summarized in the form of tables as follows:

A. For batchwise embodiments:

| Ex. No. | org solv type | org solv (pbw) | starting mat. at hrs (hrs) | addition of solvent at conv (%) | rctn time (hrs) | fin. conv (%) | fin. torq (Ncm) | cryst size M.V. (μm) | enz recv (%) |
|---|---|---|---|---|---|---|---|---|---|
| 1. | tol. | 0.145 | 11 | 55 | 18 | 92.2 | 169 | 22 | 81.5 |
| A. | — | — | — | — | 17 | 93.5 | 224 | <<10 | 34.7 |
| 2. | tol. | 0.29 | 11 | 69 | 19 | 93.9 | 80 | 65 | 89.9 |
| 3. | tol. | 0.29 | 13 | 82 | 19 | 93.5 | 135 | appr. 100 | 82.9 |
| 4. | MIBK | 0.29 | 11 | 69 | 22 | 92.5 | 78 | 53 | 89.0 |
| 5. | MIBK/tol | 0.145 | 8 | 65 | 16 | 91.8 | 84 | appr. 30 | 86.5 |
| B. | — | — | — | — | 16 | 92.1 | 243 | <<10 | 62.7 |
| 6. | tol. | 0.31 | 3 | 55 | 9 | 96.3 | 2.0 | 114 | 99.3 |
| 7. | tol. | 0.21 | 3 | 55 | 9 | 96.2 | 5.7 | 46 | 92.7 |
| 8. | tol. | 0.1 | 3 | 55 | 9 | 96.2 | 11.0 | 20 | 86.3 |
| 9. | MIBK | 0.21 | 3 | 55 | 9 | 95.8 | 0.1 | 48 | 94.1 |
| 10. | MIBK | 0.31 | 3 | 55 | 9 | 93.8 | 2.1 | 71 | 94.1 |
| 11. | NIBK | 0.1 | 3 | 55 | 9 | 93.8 | 3.0 | 24 | 87.5 |

B. For continuous embodiments:

| Ex. No. | org solv type | org solv (pbw) | at hrs (hrs) | 1st reactor conv (%) | rctn time (hrs) | 2nd reactor conv (%) | fin. torq (Ncm) | cryst size M.V. (μm) | enz recv (%) |
|---|---|---|---|---|---|---|---|---|---|
| 12. | MIBK | 0.11 | cont | 70.6 | cont | 89.9 | 3.8 | appr. 150 | 92.5 |
| 13. | tol. | 0.42 | cont | 77.6 | cont | 94.3 | 4.9 | appr. 200 | 94.4 |
| C. | — | — | — | 76.6 | cont | 90.2 | 14.7 | appr. 10 | 64.0 |

We claim:

1. A process for preparing N-protected-L-aspartyl-L-phenylalanine methyl ester by enzymatic coupling of an N-protected-L-aspartic acid with L- or DL-phenylalanine methyl ester in an aqueous solution and wherein a precipitate is formed by use of a thermolysin-like protease enzyme, which process comprises, during the course of formation of the said precipitate, adding and blending into said aqueous solution an organic solvent having a relatively high affinity for said precipitate and which, under the reaction conditions employed, is water-immiscible and forms a second liquid phase.

2. Process according to claim 1, characterized in that the organic solvent having a relatively high affinity for the precipitate is selected from the group of aromatic hydrocarbons, $C_{3-6}$ ketones, $C_{3-6}$ alcohols, $C_{1-6}$ hydrocarbon halides and $C_{2-10}$ esters, or mixtures thereof.

3. Process according to claim 1, characterized in that the amount of organic solvent added during the coupling reaction is from 0.01 to 1.0 part by weight relative to one part by weight of the sum of N-protected-L-aspartic acid and L- or DL-phenylalanine methyl ester being used in the coupling reaction.

4. Process according to claim 1, characterized in that addition to and blending with the reaction mixture of the organic solvent is started at the latest when the conversion of the coupling reaction has reached about 85%.

5. Process according to claim 19, characterized in that addition to and blending with the reaction mixture of the organic solvent is not started before the conversion of the coupling reaction has reached about 10%.

6. Process according to claim 1, characterized in that the organic solvent is toluene or methylisobutylketone, and addition to and blending with the reaction mixture of the organic solvent is started when the conversion of the coupling reaction has reached from about 30% to 75%.

7. Process according to claim 6, characterized in that the organic solvent is toluene and is added in an amount of from 0.2 to 0.5 part by weight relative to one part by weight of the sum of N-protected-L-aspartic acid and L- or DL-phenylalanine methyl ester being used in the coupling reaction.

8. Process according to claim 6, characterized in that the organic solvent is methylisobutylketone and is added in an amount of from 0.1 to 0.3 part by weight relative to one part by weight of the sum of N-protected-L-aspartic acid and L- or DL-phenylalanine methyl ester being used in the coupling reaction.

9. Process according to claim 1, characterized in that the organic solvent is continuously added to and blended with the reaction system of a continuously operated enzymatic coupling process, while precipitate is being formed.

10. Process according to claim 9, characterized in that the organic solvent is fed continuously into the first and/or further reactor(s) of a multi-reactor continuous coupling process system.

11. Process according to claim 9, characterized in that the amount of organic solvent added on average per hour during the coupling reaction is from 0.01 to 1.0 part by weight relative to one part by weight of the sum of N-protected-L- aspartic acid and L- or DL-phenylalanine methyl ester on average being used per hour in the continuous coupling reaction.

12. Process according to claim 9, characterized in that addition to and blending with the reaction mixture of the organic solvent is started at the latest when the conversion of the continuous coupling reaction first has reached about 85%.

13. Process according to claim 9, characterized in that addition to and blending with the reaction mixture of the organic solvent is not started before the conversion of the continuous coupling reaction first has reached about 10%.

14. Process according to claim 9, characterized in that the organic solvent is toluene or methylisobutylketone and addition to and blending with the reaction mixture of the organic solvent is started when the conversion of the coupling reaction first has reached from about 30% to 75%.

15. Process according to claim 14, characterized in that the organic solvent is toluene and is added in an average amount per hour of from 0.2 to 0.5 part by weight relative to one part by weight of the sum of N-protected-L-aspartic acid and L- or DL-phenylalanine methyl ester on average being used per hour in the continuous coupling reaction.

16. Process according to claim 14, characterized in that the organic solvent is methylisobutylketone and is added in an average amount per hour of from 0.1 to 0.3 part by weight relative to one part by weight of the sum of N-protected-L-aspartic acid and L- or DL-phenylalanine methyl ester on average being used per hour in the continuous coupling reaction.

17. Process according to claim 1, characterized in that the N-protected-L-aspartic acid is N-benzyloxycarbonyl-L-aspartic acid.

18. A process according to claim 1 wherein said organic solvent is selected from the group of aromatic hydrocarbons, $C_{3-6}$ ketones, $C_{3-6}$ alcohols, $C_{1-6}$ hydrocarbon halides and $C_{2-10}$ esters or mixtures thereof and is continuously added to and blended with the reaction system in a continuously operated enzymatic coupling process while the said precipitate is being formed therein.

* * * * *